(12) United States Patent
Dostie

(10) Patent No.: US 6,742,406 B2
(45) Date of Patent: Jun. 1, 2004

(54) SEDIMENT SAMPLER

(76) Inventor: Renaud Dostie, 7075 de Brunoy, Charlesbourg, Québec (CA), G1H 4H1

( * ) Notice: Subject to any disclaimer, the term of this patent is extended or adjusted under 35 U.S.C. 154(b) by 163 days.

(21) Appl. No.: 09/977,240

(22) Filed: Oct. 16, 2001

(65) Prior Publication Data
US 2002/0043117 A1 Apr. 18, 2002

(30) Foreign Application Priority Data
Oct. 17, 2000 (GB) .............................................. 0025400

(51) Int. Cl.⁷ ................................................ G01N 1/00
(52) U.S. Cl. ................................................ 73/864.64
(58) Field of Search ......................... 73/863.33, 863.41, 73/863.51, 863.52, 863.57, 864.31, 864.63, 864.64, 864.67

(56) References Cited

U.S. PATENT DOCUMENTS

| | | | | |
|---|---|---|---|---|
| 232,519 A | * | 9/1880 | Lindsay | 73/864.65 |
| 4,157,664 A | * | 6/1979 | Robinson | 73/864.64 |
| 4,563,896 A | * | 1/1986 | Arnold | 73/864.51 |
| 4,762,009 A | * | 8/1988 | Scrudto | 73/864.51 |

* cited by examiner

Primary Examiner—Robert Raevis

(57) ABSTRACT

A sediment collecting device for collecting sediments in a body of liquid. The device includes a collecting container. The peripheral wall of the collecting container is provided with a plurality of collecting apertures. An obstructing is inserted into the collecting container. The obstructing container has a peripheral wall provided with a plurality of valve apertures. The valve apertures are configured, sized and positioned so that when the obstructing container is in an open configuration the valve apertures are in register with the collecting apertures and so that when the obstructing container is in a closed configuration the valve apertures are offset relative to the collecting apertures. The device also includes a carrying container configured and sized for receiving the collecting container and carrying container lid. The carrying container lid is attachable to the carrying container upper peripheral edge for forming together with the collecting container a collecting enclosure. The carrying container lid is also attachable to the collecting container base wall for acting as an anchoring component for the device.

9 Claims, 8 Drawing Sheets

SEDIMENT SAMPLER

FIELD OF THE INVENTION

The present invention relates to the general field of samplers and is particularly concerned with a sediment sampler.

BACKGROUND OF THE INVENTION

Increased concerns for environmental issues has led to a concurrent demand for improved environment monitoring methods and devices. Some of the environment monitoring methods are based upon the monitoring of the sedimentation of bodies of water. Indeed, both suspended and bottom sediments may prove to be a valuable source of information related to the ecological health of various types of bodies of water such as streams, rivers, lakes, pounds or the like.

In particular, because of the major repercussions resulting from increased levels of bottom sediment it is highly desirable to evaluate and monitor the impact on the level of sediments created by the construction of man-made structures adjacent certain types of bodies of water such as streams or rivers. The dumping of numerous waste forms in shallow water, as well as dredging and other engineering activities, places large quantities of sediments and polluting substances in suspension. These substances are subsequently carried away to different parts of the water body by the action of currents. Many problems related to waste disposal, channel and harbor dredging, off shore drilling and other engineering projects required detail knowledge of the motion of suspended sediments.

Some of the problems generated by increased sediment density directly affect various life forms. For example, in it is well known that sedimentation may proved to be detrimental to the reproduction cycle of certain types of fish. Indeed, during the mating period, some fish species typically dig a nest in the gravel forming the bed of some rivers. Once the nest has been digged the eggs are laid and covered with a layer of gravel by the fish. Survival of the fish eggs requires proper oxygen supply. This oxygen supply is normally supplied by the flow of water through the gravel.

If the quantity of fine sediment increases adjacent the nesting region the oxygen supply to the eggs may suffer. Indeed, relatively fine sediments have a tendency to lodge in the gravel bed and to potentially block the through flow of water. Reduced water flow in the gravel, in turn, prevents adequate oxygen supply to the fish eggs. Since fine sediments often remain in the gravel for several years the problem often persists with sometimes important consequences.

Some prior art devices specifically designed for monitoring bottom sediments have been proposed in the prior art. However, most of these prior art devices suffer from several major drawbacks. For example, one prior art method involves the use of a bucket-type container or a bag filled with sampling gravel and buried in the riverbed. After a predetermined period of time the contains of the bucket or bag is removed and washed in order to evaluate the type and quantity of sediments that have settled in the sampling gravel. This method however only provide a rough estimate of sediment accumulation since sediments that would reach the sampling volume through lateral movement instead of vertical dropping are excluded. Also, these prior art devices may be sealed of by the dropping sediments.

Furthermore, the prior art devices also often suffer from the fact during withdrawal from the sampling area some of the sediments have a tendency to fall out of the sediment sampler hence, again affecting the accuracy of the sampling procedure. Still further, some prior art sediment samplers are particularly difficult to anchor to the bottom surface of bodies of water in such a manner that they remain stable during the sampling period. Accordingly, there exists a need for an improved sediment sampler.

SUMMARY OF THE INVENTION

In accordance with an embodiment of the invention, there is provided a sediment collecting device for collecting sediments in a body of liquid, the body of liquid defining a top surface and a bottom floor, the device comprising: a collecting container, the collecting container defining a collecting container base wall and a collecting container peripheral wall extending from the collecting container base wall, the collecting container peripheral wall being provided with a collecting aperture extending therethrough; an obstructing means positioned substantially adjacent the collecting aperture for selectively obstructing the collecting aperture, the obstructing means being movable between an open configuration allowing the sediments to flow through the collecting aperture and a closed configuration preventing the sediments from flowing through the collecting aperture; an anchoring means attached to the collecting container for anchoring the collecting container to the bottom floor of the body of water.

Preferably, the collecting container peripheral wall has a generally frustro-conical configuration and is provided with a plurality of collecting apertures extending therethrough, the collecting apertures being configured, sized and positioned so as to allow though flow of the liquid across the collecting container peripheral wall.

Conveniently, the device further comprises a carrying container configured and sized for receiving the collecting container, the carrying container defining a carrying container base wall and a carrying container peripheral wall extending from the carrying container base wall, the carrying container peripheral wall defining a carrying container peripheral edge; the device further including a carrying container lid, the carrying container lid being attachable to the carrying container upper peripheral edge for forming together with the collecting container a collecting enclosure, the carrying container lid being also attachable to the collecting container base wall for forming at least part of the anchoring means.

Preferably, the carrying container lid is attached to the collecting container base wall by a generally elongated attachment component extending through both the collecting container base wall and the carrying container lid, the attachment component protruding outwardly from the carrying container lid so as to form at least part of the anchoring means.

Conveniently, the obstructing means includes an obstructing container, the obstructing container being configured and sized so as to be at least partially insertable into the collecting container, the obstructing container defining an obstructing container base wall and a peripheral obstructing wall extending from the obstructing container base wall, the obstructing wall being provided with a valve aperture extending therethrough, the valve aperture being configured, sized and positioned so that when the obstructing means is in the open configuration the valve aperture is at least partially in register with the collecting aperture and so that when the obstructing means is in the closed configuration preventing the valve aperture is offset relative to the collecting aperture.

Preferably, the device further comprises a positioning means for facilitating the positioning of the obstructing means between the closed and open configurations and a localizing means for facilitating the localization of the device when the latter is immersed in the body of liquid.

Advantages of the present invention include that the proposed sediment sampler provides a novel and improved device for measuring the sedimentation in bodies of water such as oceans, lakes, estuaries, lagoons, reservoir and the like. The proposed device is specifically designed so as to increase the accuracy of the sampling procedure.

Also, the proposed sediment sampler is designed so as to allow the sampling of sediments traveling in at least two generally perpendicular directions. The proposed sediment sampler allows for the collection of sediments dropping substantially vertically towards the bottom of the body of water as well as for the collection of sediments that are traveling in a direction substantially parallel to the bottom of the body of water.

Furthermore, the proposed sediment sampler is specifically designed so as to reduce the risks of losing trapped sediments during removal of the sediment sampler on the sampling site and during transportation of the sediments to remote locations such as an analyzing laboratory. The proposed sediment sampler is further specifically designed so as to facilitate its installation at the sampling site and its removal from its sampling site through a set of simple and ergonomic steps without requiring special tooling or manual dexterity.

Also, the proposed sediment sampler is provided with anchoring features that allow the sediment sampler to be stably anchored to the bottom of the body of water therefore reducing the risk of having the sediment sampler washed away from the sampling site during the sampling period.

Still further, the proposed sediment sampler is specifically so as to be easily located once installed at the sampling site. It is also designed so as to be reusable and easily washable. Furthermore, the proposed sediment sampler is also designed so as to reduce required storage space when not in use.

Furthermore, the proposed sediment sampler is designed so as to conform to conventional forms of manufacturing therefore providing a sediment sampler that is economical, long lasting and relatively trouble free in operation.

BRIEF DESCRIPTION OF THE DRAWINGS

An embodiment of the present invention will now be disclosed, by way of example, in reference to the following drawings in which.

DETAILED DESCRIPTION OF THE INVENTION

Figure 1:
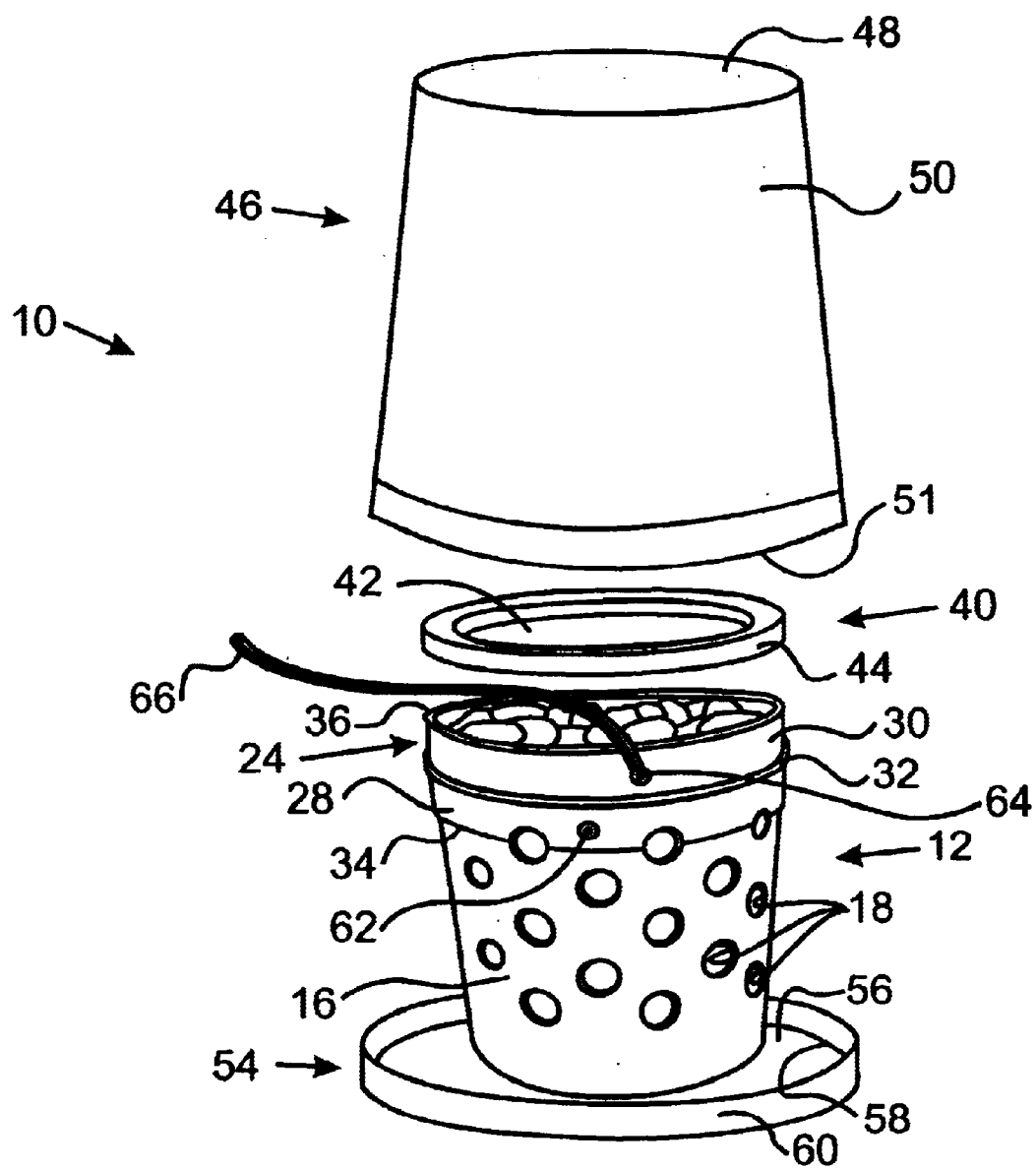
FIG. 1: in a partially exploded perspective view illustrates a sediment collecting device in accordance with an embodiment of the present invention.

Referring to FIG. 1, there is shown a sediment collecting device 10 in accordance with an embodiment of the present invention. The sediment collecting device 10 includes a collecting container 12 shown in greater details in FIG. 2. The collecting container 12 defines a collecting container base wall 14 and a collecting container peripheral wall 16 extending from the collecting container base wall 14. The collecting container peripheral wall 16 is provided with at least one collecting aperture 18 extending therethrough.

Figure 4:
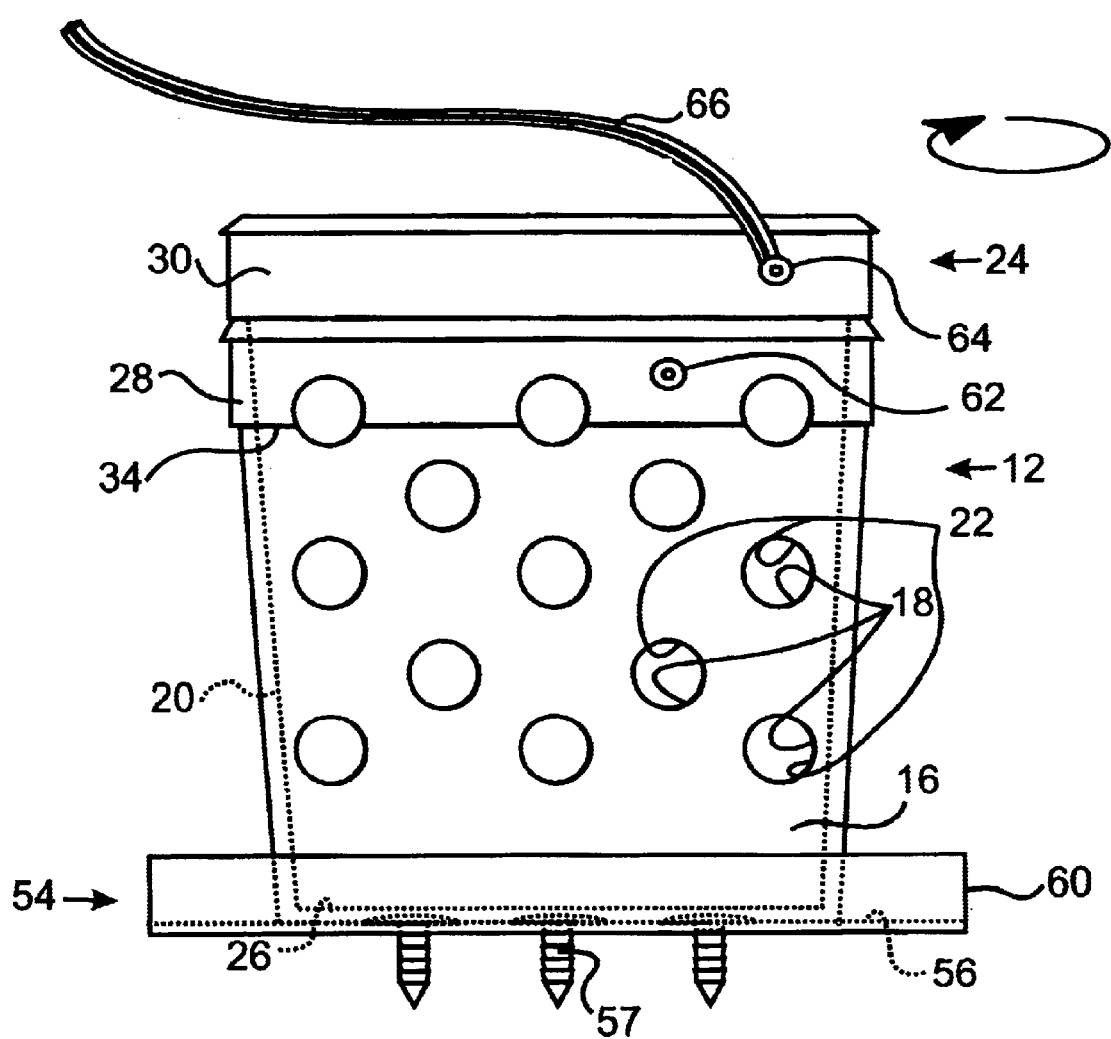
FIG. 4: in an elevational view illustrates an obstructing container being rotated in a closed configuration relative to a collecting container both the carrying and collecting containers being part of a sediment collecting device in accordance with an embodiment of the present invention.
Figure 5:
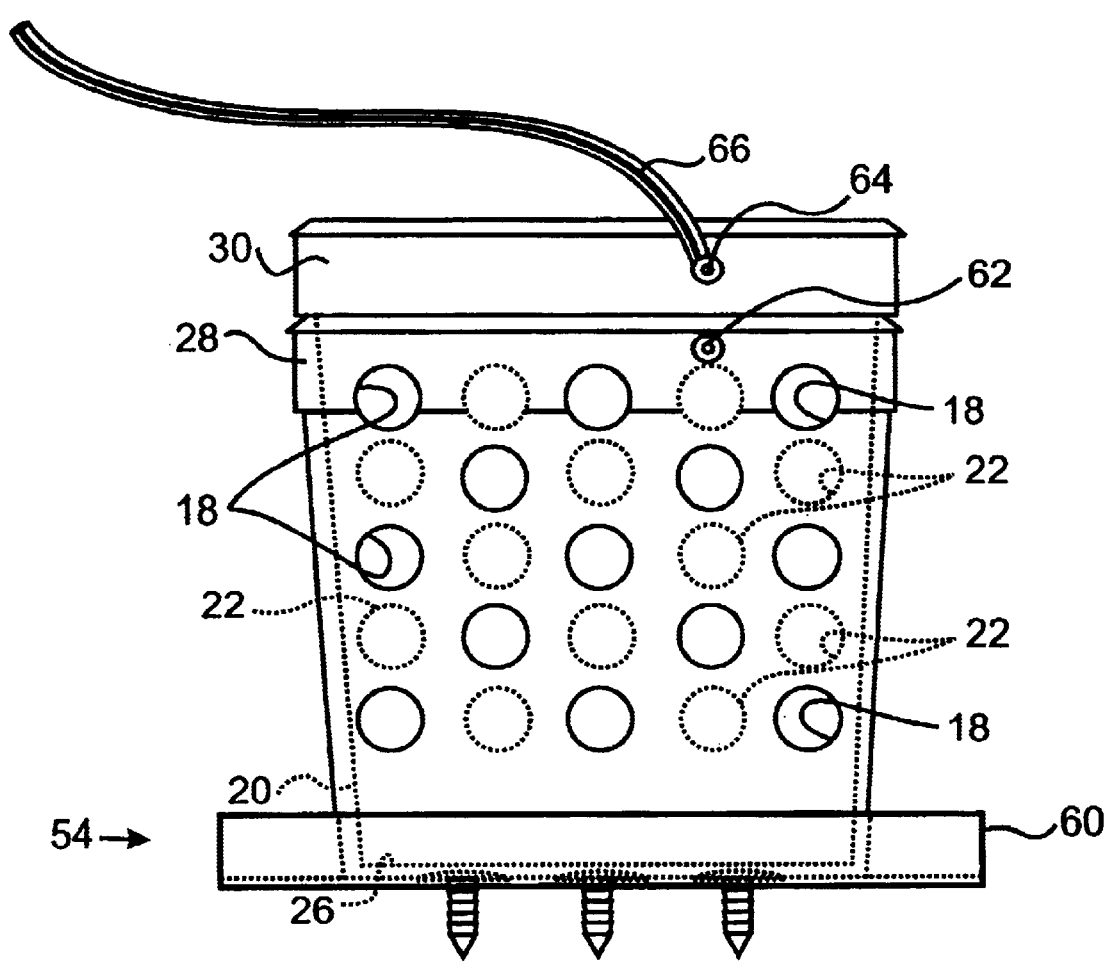
FIG. 5: in an elevational view illustrates an obstructing container in an opened configuration relative to a collecting container both the carrying and collecting containers being part of a sediment collecting device in accordance with an embodiment of the present invention.

The sediment collecting device 10 also includes an obstructing means positioned substantially adjacent to the collecting aperture 18 for selectively obstructing the collecting aperture 18. The obstructing means is moveable between an opened configuration shown in FIG. 5 allowing sediments suspended in a body of water to flow through the collecting aperture 18 and a closed configuration shown in FIG. 4 preventing the sediments suspended in a body of water from flowing through the collecting aperture 18.

The sediment collecting device 10 also includes an anchoring means attached to the collecting container 12 for anchoring the collecting container 12 to the bottom floor of a body of water. The obstructing means and the anchoring means may take various forms, some of which are hereinafter disclosed in greater details, without departing from the scope of the present invention.

Typically, the collecting container peripheral wall 16 is provided at least two collecting apertures 18 extending therethrough. The collecting apertures 18 are configured, sized and positioned so as to allow through flow of suspended sediments between the collecting apertures 18. Typically, also, the collecting apertures 18 are in a generally diametrically opposed relationship relative to each other.

In the preferred embodiment shown throughout the figures, the collecting container peripheral wall 16 is provided with a plurality of collecting apertures 18 extending therethrough. The collecting apertures 18 are configured, sized and positioned so as to allow sediments to flow laterally or radially into the collecting container 12 from various angles. Typically, although by no means exclusively, each collecting aperture 18 has a generally disc-shaped configuration and an external diameter substantially in the range of 1.2 cm. Also, preferably, the collecting apertures 18 are aligned in a matrix forming rows and columns so as to facilitate interaction with the obstructing means as will be hereinafter disclosed in greater details. Typically although by no means exclusively the matrix is formed by a set of 40 apertures disposed in rows and columns forming a substantially helicoidally shaped pattern for interacting with the obstructing means as will be hereinafter disclosed in greater details.

The obstructing means typically includes an obstructing wall 20 positioned adjacent the collecting container peripheral wall 16. The obstructing wall 20 is provided with at least one valve aperture 22 extending therethrough for collaborating with at least one collecting aperture 18. The valve aperture 22 is configured, sized and positioned so that when the obstructing means is in the opened configuration the valve aperture 22 at least partially in register with the collecting aperture 18. The valve aperture 22 is also configured, sized and positioned so that when the obstructing means is in the closed configuration the valve aperture 22 is offset relative to the collecting aperture 18 thus preventing the flow of water through the collecting aperture 18.

Figure 3:
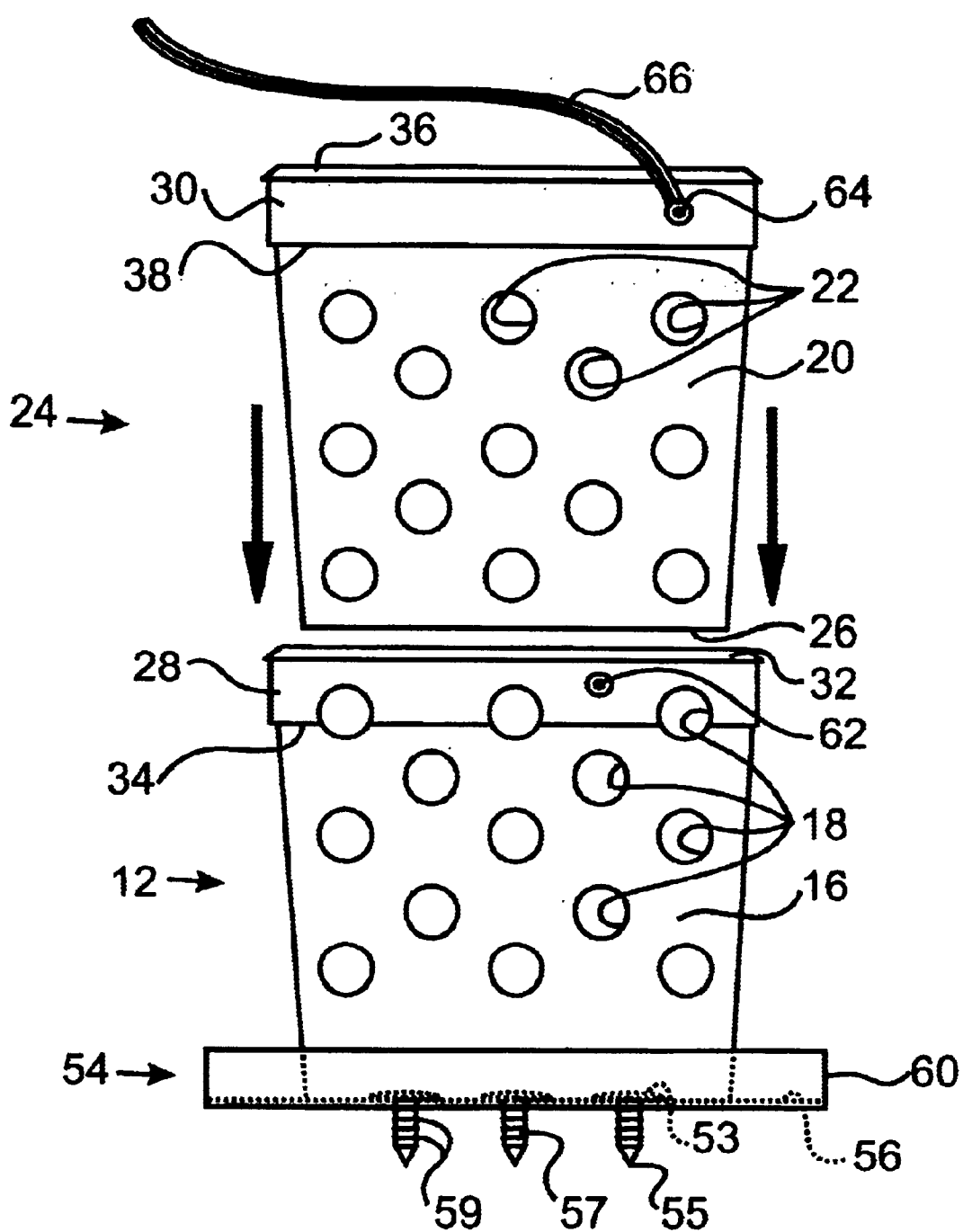
FIG. 3: in an elevational view illustrates an obstructing container about to be inserted within a collecting container attached to a carrying container lid, the obstructing container also being part of a sediment collecting device in accordance with an embodiment of the present invention.

Preferably, as shown more specifically in FIG. 3, the obstructing wall 20 is part of an obstructing container 24 being the peripheral wall of the obstructing container 24. The obstructing container 24 typically although by no means necessarily further includes an obstructing container base wall 26. The obstructing container 24 is typically configured and sized so as to be at least partially insertable into the collecting container 12. Preferably, both the collecting container peripheral wall 16 and the obstructing wall 20 have a generally frustro-conical configuration and have substantially similar dimensions so that the obstructing container 24 is substantially fittingly insertable into the collecting container 12 as illustrated in FIGS. 4 through 7.

Preferably, the upper peripheral edges of the collecting container peripheral wall 16 and the obstructing wall 20 are respectively provided with a collecting container rim 28 and an obstructing container rim 30. The collecting container rim 28 defines a collecting container rim first edge 32 and a collecting container rim second edge 34. Similarly, the obstructing container rim 30 defines an obstructing container rim first edge 36 and an obstructing container rim second edge 38. When the obstructing container 24 is inserted into the collecting container 12 the obstructing container rim second edge 38 is adapted to abuttingly contact with the collecting container rim first edge 32 and to allow relative rotation between the collecting container 12 and the obstructing container 24.

The sediment collecting device 10 is preferably further provided with a collecting lid 40 for sealing off the open top surface of the collecting container 12 and/or the obstructing container 24. In the preferred embodiment of the invention shown throughout the figures wherein the obstructing means includes the obstructing container 24 fittingly inserted within the collecting container 12, the collecting lid 40 is configured and sized for being mounted to the obstructing container first rim 36.

The collecting lid 40 is typically provided with a substantially disc-shaped collecting lid wall 42 having a peripheral collecting lid flange 44. The collecting lid flange 44 is adapted to be snappily mounted to the obstructing container rim first flange 36 in a conventional manner. The contact between the obstructing container rim second edge 38 and the collecting container rim first edge 32 preferably defines a seal tight link between the collecting container 32 and the obstructing container 24. Hence, when the obstructing container 24 is inserted within the collecting container 12 in a closed configuration and the collecting lid 42 is mounted over the obstructing container 24, water and sediments contained within the collecting and obstructing containers 12, 24 are prevented from linking out.

The sediment collecting device 10 typically still further includes a carrying container 46. The carrying container 46 is configured and sized for receiving the collecting container 12. In the embodiment wherein the obstructing means includes the obstructing container 24, the carrying container 46 is configured and sized for receiving both the collecting container 12 and the obstructive container 24. The carrying container 46 defines a carrying container base wall 48 and a carrying container peripheral wall 50 extending from the carrying container base wall 48.

The carrying container peripheral wall 50 defines a carrying container peripheral edge 52. The carrying container 46 is an open-type container defining an aperture adapted to be sealed off by a carrying container lid 54. The carrying container lid 54 is attachable to the carrying container peripheral edge 52 in a conventional manner so that the carrying container lid 54 together with the carrying container 46 form a carrying enclosure for receiving the collecting container 12.

Typically, although by no means exclusively, the carrying container peripheral wall 50 has a generally frustro-conical configuration and the carrying container 46 defines a carrying container volume having a value substantially in the range of twice the volume of the collecting container 12.

Typically, the carrying container lid 54 is designed so as to be attachable not only to the carrying container peripheral edge 52 but also to the collecting container base wall 14 for forming at least part of the anchoring means. As shown more specifically in FIGS. 2 through 8, the carrying container lid 54 is preferably attached to the collecting container base wall 14 by at least one and preferably a plurality of generally elongated attachment components 52 extending through both the collecting container base wall 14 and the carrying container lid 54. The attachment components 52 are configured and sized so as to protrude outwardly from the carrying container lid 54 when the latter is attached to the collecting container base wall 14 so that the carrying container lid 54 may act as at least part of the anchoring means.

Typically, each attachment components 52 is provided with a generally pointed tip 55 and defines a generally elongated stem 57 provided with at least one and preferably a plurality of stem lateral protrusions 59 extending laterally therefrom. The pointed tip 55 is adapted to facilitate the penetration of the attachment components 52 into both the carrying container lid 54 during assembly and into the floor of the body of liquid during anchorage of the sediment collecting device 10 thereto. The lateral protrusion 59 preferably take the form of circumferential ribs and are adapted to increase the frictional force between the stem 57 and both the carrying container lid 54 and the material forming the floor of the body of water to which the sediment collecting device 10 is anchored. The attachment components 52 are preferably provided with attachment component heads 64 adapted to abuttingly contact the inner surface of the collecting container base wall 14.

Preferably, the carrying container lid 54 defines an attachment section located so as to be substantially in register with the collecting container base wall 14 and attached thereto. The carrying container lid 54 also defines an anchoring section 56 protruding laterally from the attachment section and thus from the collecting container base wall 14 when the carrying container lid 54 is attached to the collecting container base wall 14.

Typically, the carrying container lid 54 has a generally disc-shaped configuration defining a generally centrally disposed and disc-shaped attachment section and a generally annular anchoring section 56 extending radially from the attachment section.

Typically, the anchoring section 56 defines an anchoring section peripheral edge 58. The carrying container lid 54 preferably further includes a lid rim 60 extending substantially perpendicularly from the anchoring section peripheral edge 58. The anchoring section 56 together with the lid rim 60 are adapted to act as an annular tray for receiving gravel or other suitable material for further anchoring the sediment collecting device 10 to the bottom floor of the body of liquid.

The sediment collecting device 10 preferably further includes a positioning means for facilitating the positioning of the obstructing means between the closed and opened configurations. In the preferred embodiment, the positioning means is adapted to facilitate the accurate relative positioning between the collecting container 12 and the obstructing container 24 so that their respective collecting and valve apertures 18, 22 may be put selectively in an offset or registered relationship relative to each other without the need for axially displacing the collecting and obstructing containers 12, 24 relative to each other.

In a preferred embodiment of the invention, the positioning means includes a first and second indicia respectively marked on the collecting container rim 28 and the obstructing container rim 30. The first and second indicia are respectively positioned on the collecting container rim 28 and the obstructing container rim 30 so as to when the first and second indicia are substantially in register with each other the obstructing means is in either one of the predetermined opened or closed configuration. Preferably, the first and second indicia take the form of first and second marking pins 62, 64.

The sediment collecting device 10 is preferably further provided with a localizing means for facilitating the localization of the sediment collecting device 10 when the latter is anchored to the floor surface of the body of liquid. Typically, the localizing means includes a strip 66 of relatively buoyant material attached to the sediment collecting device 10 for floating from the device 10 towards the surface of the body of liquid.

Typically, though by no means exclusively, the collecting container 12 has an internal volume substantially in the range of 1 liter. Also, typically, although by no means exclusively, the collecting container has a height substantially in the range of 13.5 cm and an average diameter substantially in the range of 12 cm. Furthermore, typically, although by no means exclusively, the collecting aperture 18 together form a total opening having an area substantially in the range of 70 cm$^2$. Typically, although by no means exclusively, all three containers are made out of high-density polyethylene while all lids are made out of low-density polyethylene.

Figure 2:
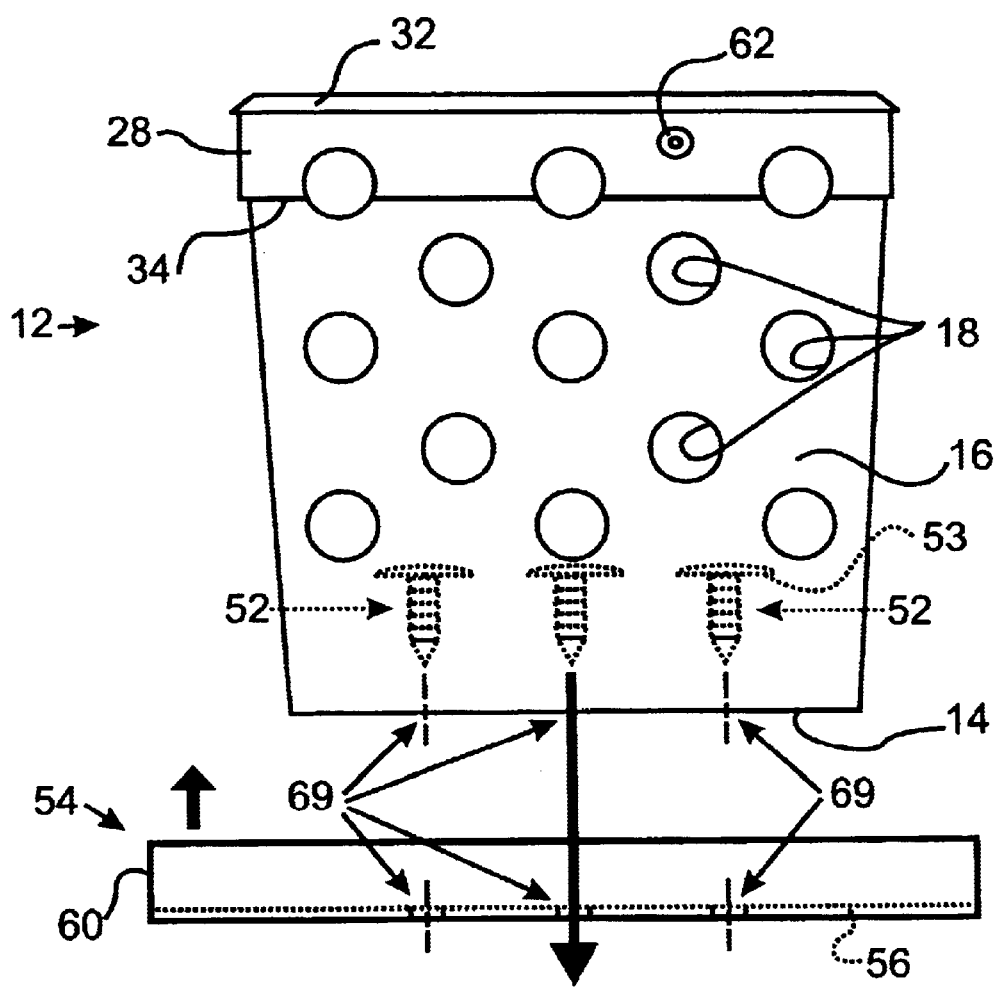
FIG. 2: in an elevational view illustrates a carrying container about to be secured to the carrying container lid, both the collecting container and the carrying container lid being part of a sediment collecting device in accordance with an embodiment of the present invention.

Typically, prior to actually using the sediment collecting device 10 the latter must be assembled although it could be manufactured and sold in an assembled state. As shown in FIG. 2, when the sediment collecting device 10 is sold unassembled, the carrying container lid 54 is first attached to the collecting container bottom wall 14 by inserting the stems 57 into optional stem apertures 62 formed in the attachment section of the carrying container base wall 56.

As shown in FIG. 3, the obstructing container 24 is then inserted within the collecting container 12 until the obstructing container rim second edge 38 abuttingly contacts the collecting container rim first edge 32. The collecting and obstructing containers 12, 14 are then rotated relative to each other towards their closed configurations illustrated in FIG. 4 wherein the collecting and valve apertures 18, 22 are offset relative to each other thus preventing the flow of liquid through the collecting aperture 18. Monitoring of the relative positioning between the collecting and valve apertures 18, 22 is facilitated by the monitoring of the relative positioning between the first and second positioning pins 62, 64.

Once the sediment collecting device 10 is in its closed configuration the obstructing container 24 is filled with clean gravel or other suitable substrate for collecting the sediments. The assembled sediment collecting device 10 is brought to the sampling location and a cavity is digged in the bed of the body of liquid at a predetermined sampling site. The cavity typically has a diameter substantially in the range of 15 cm and a height substantially in the range of 18 cm. The bottom of the cavity is preferably lined with a layer of gravel in order to minimize free space between the sediment collecting device 10 and the bottom of the cavity. The collecting and obstructing containers 12, 24 are then pivoted relative to each other towards their opened configuration shown in FIG. 5 wherein the collecting and valve apertures 18, 22 are substantially in register with each other allowing through flow of liquid from outside the sediment collecting device 10 towards the clean sampling gravel located inside the obstructing container 24.

Once the sediment collecting device 10 is in its opened configuration the sediment collecting device 10 is positioned within the cavity formed in the bed of the body of liquid. Clean gravel or other suitable weighted material is then deposited in the anchoring section 56 between the outer surface of the collecting container peripheral 16 and the lid rim 60.

Once the sediment collecting device 10 is suitably positioned within the cavity formed in the bed of the body of water the localizing strip 66 is positioned so as to allow visualization thereof at the surface of the body of water. Optionally, a fine layer of gravel substantially identical to that at the bottom of the body of water is poured on top of the volume of gravel contained within the obstructing container 24.

Figure 6:
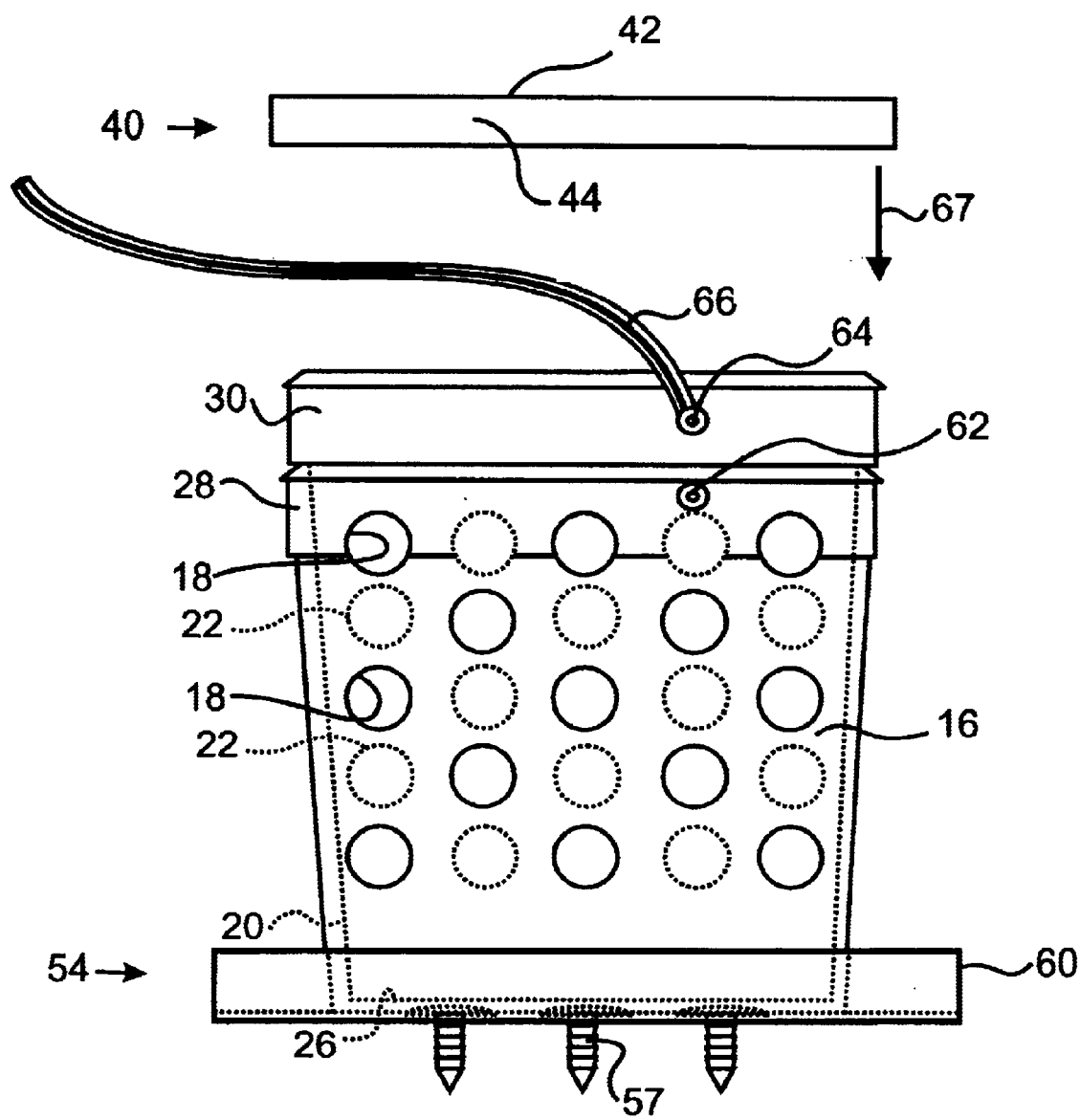
FIG. 6: in an elevational view illustrates a collecting lid about to be mounted on the rim of an obstructing container part of a sediment collecting device in accordance with an embodiment of the present invention.

The sediment collecting device 10 is allowed to collect sediments for a predetermined period of sampling time that may vary depending on the research criteria. Once this predetermined period of sampling time has elapse, the optional layer of small gravel overriding the sediment collecting device 10 is removed. As shown in FIG. 6 and indicated by arrow 67 the collecting lid 40 is then sealingly engaged with the obstructing container rim 30 so as to seal off the opening over the obstructing container 24. The obstructing container 24 is then pivoted back towards the device closed configuration preferably with the help of the first and second positioning pins 62, 64.

The sediment collecting device 10 is then carefully removed from the body of water typically while maintaining a manual pressure on the collecting lid 40 to ensure a seal tight fit. Gravel and/or other granular material located in the anchoring section 56 is carefully removed typically by slightly oscillating the sediment collecting device 10.

Figure 7:
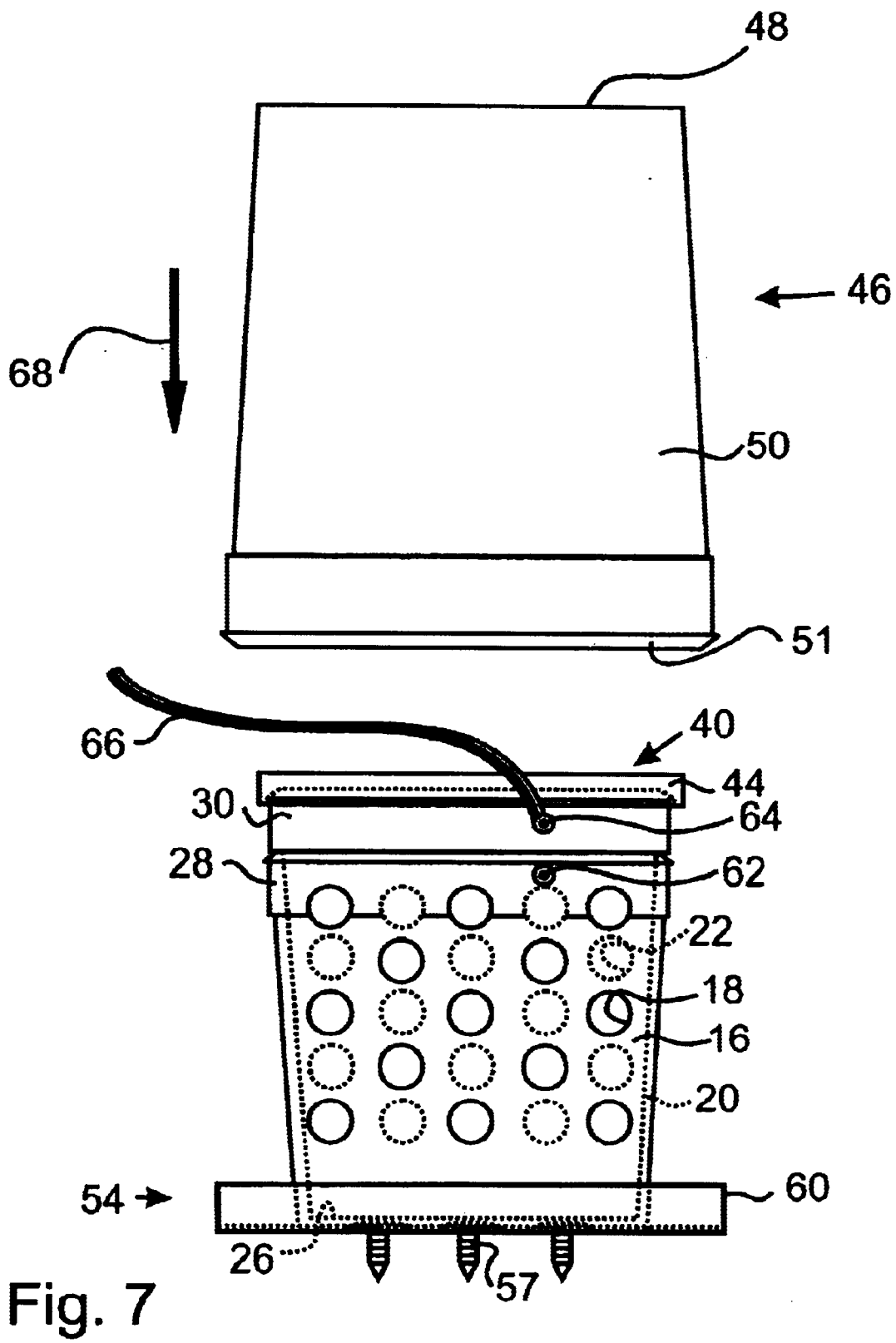
FIG. 7: in an elevational view illustrates a carrying container about to be mounted over a collecting container both the carrying and collecting containers being part of a sediment collecting device in accordance with an embodiment of the present invention.

As shown in FIG. 7 and indicated by arrow 68 the carrying container 46 in an inverted position is inserted over the collecting and obstructing containers 12, 14. The carrying container peripheral edge 52 then sealingly engages the carrying container lid 54 in order to form a seal tight enclosure for the collecting and obstructing containers 12, 14 and the sediment contained therein.

Figure 8:
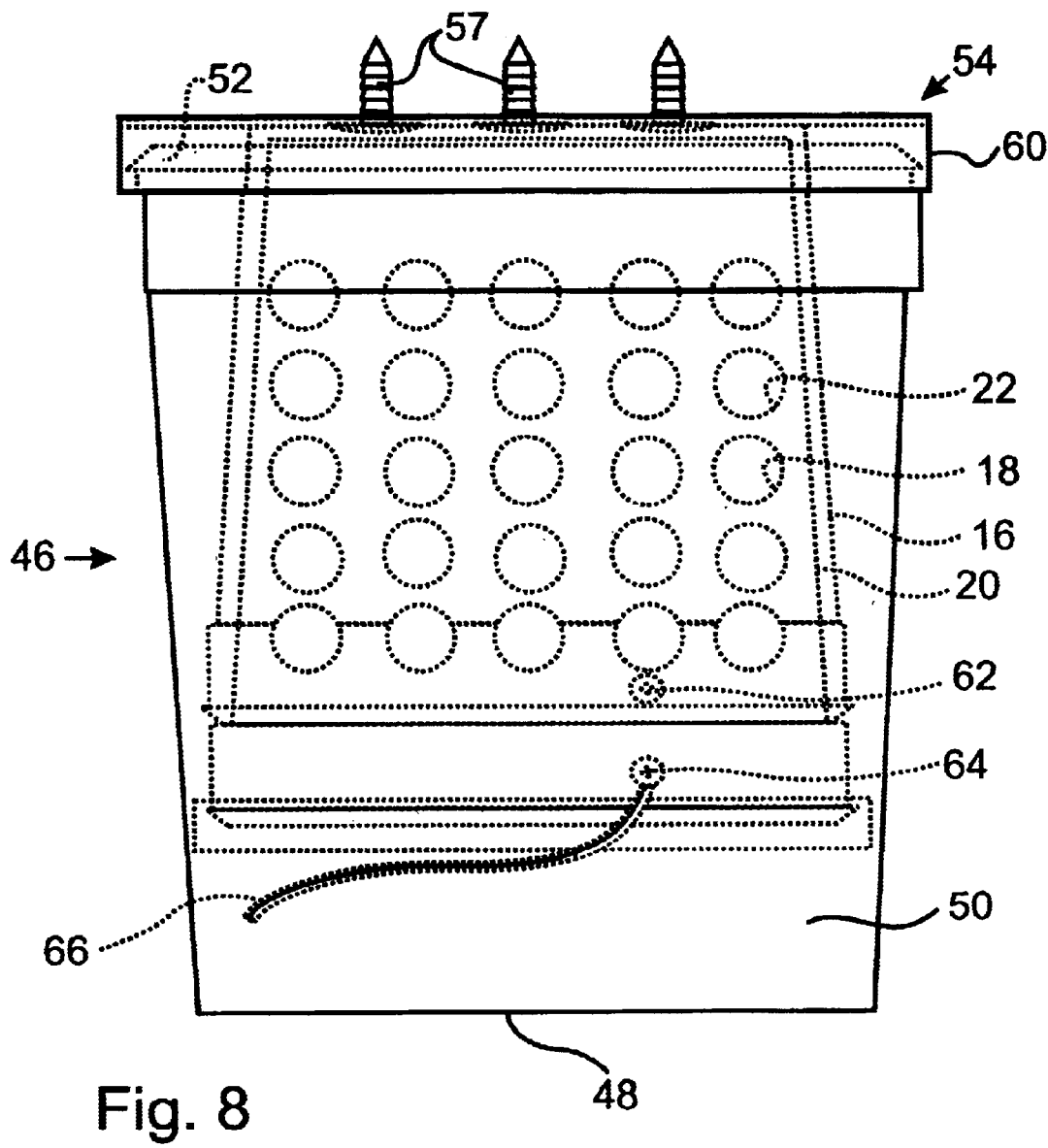
FIG. 8: in an elevation view illustrates a sediment collecting device in accordance with an embodiment of the present invention, the sediment collecting device being shown in a carrying configuration, internal components of the sediment collecting device being shown in phantom lines.

Once the carrying container 46 forms a seal tight enclosure, it may be pivoted as shown in FIG. 8 and prepared for shipping to analyzing sites such as a remote laboratory. Once the sediment collecting device 10 has reached the analyzing site the carrying container lid 54 merely needs to be removed in order to access the sediments trapped in the gravel contained within the obstructing container 24.

The embodiments of the invention in which an exclusive privilege or property is claimed are defined as follows:

1. A sediment collecting device for collecting sediments in a body of liquid, said body of liquid defining a top surface and a bottom floor, said device comprising:
   a collecting container said collecting container defining a collecting container base wall and a collecting container peripheral wall extending from said collecting container base wall, said collecting container peripheral wall being provided with a collecting aperture extending therethrough;
   an obstructing means positioned substantially adjacent said collecting aperture for selectively obstructing said collecting aperture, said obstructing means being movable between an open configuration allowing said sediments to flow through said collecting aperture and a closed configuration preventing said sediments from flowing through said collecting aperture;
   an anchoring means attached to said collecting container for anchoring said collecting container to said bottom floor of said body of liquid;
   a carrying container configured and sized for receiving said collecting container, said carrying container defining a carrying container base wall and a carrying container peripheral wall extending from said carrying container base wall, said carrying container peripheral wall defining a carrying container peripheral edge; said device further including a carrying container lid, said carrying container lid being attachable to said carrying container upper peripheral edge for forming together with said collecting container a collecting enclosure, said carrying container lid being also attachable to said collecting container base wall for forming at least part of said anchoring means.

2. A device as recited in claim 1 wherein said carrying container lid is attached to said collecting container base wall by a generally elongated attachment component extending through both said collecting container base wall and said carrying container lid, said attachment component protruding outwardly from said carrying container lid so as to form at least part of said anchoring means.

3. A device as recited in claim 2 wherein said attachment component has a generally pointed tip.

4. A device as recited in claim 2 wherein said attachment component defines an elongated stem, said elongated stem being provided with at least one stem lateral protrusion extending laterally from said stem.

5. A device as recited in claim 1 wherein said carrying container lid defines an attachment section and an anchoring section, said attachment section being substantially in register with said collecting container base wall when attached thereto, said anchoring section protruding laterally from said collecting container base wall when said carrying container lid is attached to said collecting container base wall.

6. A device as recited in claim 5 wherein said carrying container lid has a generally disc-shaped configuration defining a generally centrally disposed and disc-shaped attachment section and a generally annular anchoring section extending radially from said attachment section.

7. A device as recited in claim 6 wherein said anchoring section defines an anchoring section peripheral edge and wherein said container lid further includes a lid rim extending substantially perpendicularly from said anchoring section peripheral edge.

8. A sediment collecting device for collecting sediments in a body of liquid, said body of liquid defining a top surface and a bottom floor, said device comprising:
   a collecting container, said collecting container defining a collecting container base wall and a collecting container peripheral wall extending from said collecting container base wall, said collecting container peripheral wall being provided with a collecting aperture extending therethrough;
   an obstructing means positioned substantially adjacent said collecting aperture for selectively obstructing said collecting aperture, said obstructing means being movable between an open configuration allowing said sediments to flow through said collecting aperture and a closed configuration preventing said sediments from flowing through said collecting aperture;
   an anchoring means attached to said collecting container for anchoring said collecting container to said bottom floor of said body of liquid;
   said obstructing means including an obstructing container, said obstructing container being configured and sized so as to be at least partially insertable into said collecting container, said obstructing container defining an obstructing container base wall and a peripheral obstructing wall extending from said obstructing container base wall, said obstructing wall being provided with a valve aperture extending therethrough, said valve aperture being configured, sized and positioned so that when said obstructing means is in said open configuration said valve aperture is at least partially in register with said collecting aperture and so that when said obstructing means is in said closed configuration said valve aperture is offset relative to said collecting aperture;
   the peripheral edge of said collecting container peripheral wall and said obstructing wall being respectively provided with a collecting container rim and an obstructing container rim, said collecting container rim defining a collecting container rim first edge and a collecting container rim second edge, said obstructing container rim defining an obstructing container rim first edge and an obstructing container rim second edge, said obstructing container rim second edge abuttingly contacting said collecting container rim first edge when said obstructing container is inserted into said collecting container.

9. A sediment collecting device for collecting sediments in a body of liquid, said body of liquid defining a top surface and a bottom floor, said device comprising:
   a collecting container, said collecting container defining a collecting container base wall and a collecting container peripheral wall extending from said collecting container base wall, said collecting container peripheral wall being provided with a collecting aperture extending therethrough;
   an obstructing means positioned substantially adjacent said collecting aperture for selectively obstructing said collecting aperture, said obstructing means being movable between an open configuration allowing said sediments to flow through said collecting aperture and a closed configuration preventing said sediments from flowing through said collecting aperture;
   an anchoring means attached to said collecting container for anchoring said collecting container to said bottom floor of said body of liquid;
   a localizing means for facilitating the localization of said device when the latter is immersed in said body of liquid;
   said localizing means including a strip of relatively buoyant material attached to said device for floating from said device towards said surface of said body of liquid.

* * * * *